United States Patent [19]

Khanna et al.

[11] 4,329,461

[45] May 11, 1982

[54] FLUORESCENT THYROID HORMONE CONJUGATES AND THEIR USES

[75] Inventors: Pyare L. Khanna, San Jose; Edwin F. Ullman, Atherton, both of Calif.

[73] Assignee: Syva Company, Palo Alto, Calif.

[21] Appl. No.: 111,158

[22] Filed: Jan. 11, 1980

[51] Int. Cl.³ .................. C07D 405/12; A61K 31/495
[52] U.S. Cl. ........................................ 544/375; 424/8; 544/300; 549/388; 549/223
[58] Field of Search .......................................... 544/375

[56] References Cited

U.S. PATENT DOCUMENTS

| | | | |
|---|---|---|---|
| 3,200,120 | 8/1965 | Lovell | 544/375 |
| 3,901,645 | 8/1975 | Gross | 424/1 |
| 3,992,631 | 11/1976 | Harte | 424/12 |
| 3,996,345 | 12/1976 | Ullman et al. | 424/12 |
| 3,998,943 | 12/1976 | Ullman | 424/12 |
| 4,067,959 | 1/1978 | Bolz | 424/1 |
| 4,160,818 | 7/1979 | Smith et al. | 424/8 |

*Primary Examiner*—Glennon H. Hollrah
*Assistant Examiner*—James H. Turnipseed
*Attorney, Agent, or Firm*—Bertram I. Rowland

[57] ABSTRACT

Novel polyhalothyronines or immunogenic mimetic analogs are provided conjugated to a fluorescer compound with the resulting conjugate being highly fluorescent. Specifically, the compounds have at least one of the following characteristics: bromine(s) at the 3',5'-positions of the thyronine or mimetic analog; or a rigid linking group between the thyronine and the fluorescer, so as to inhibit heavy atom catalyzed decay of fluorescence. The subject conjugates find a wide variety of uses in detecting for thyroid hormones as well as proteins which specifically bind to thyroid hormones.

9 Claims, No Drawings

FLUORESCENT THYROID HORMONE CONJUGATES AND THEIR USES

BACKGROUND OF THE INVENTION

1. Field of the Invention

The subject compound find use in immunoassays as well as labeling of proteins which have a specific affinity for thyroid hormones.

2. Brief Description of the Prior Art

Fluorescent assays may be found in U.S. Pat. Nos. 3,901,654, 3,998,943, 3,996,345, and 4,067,959 which describe a variety of ways of performing fluorometric assays. In each instance, to the extent that a heavy atom compound is involved, fluroescence is quenched by the conjugate of the heavy atom compound to the fluorescer. Smith, FEBS Letters, 77, 25 (1977) discloses that binding of anti-thyroxin to a thyroxine-fluorophore conjugate results in fluorescent enhancement.

SUMMARY OF THE INVENTION

Novel fluorophore-thyroxine conjugates are provided which are fluorescent and do not display significant heavy atom catalyzed radiationaless decay of fluorescence. The compounds involve 3,5-diiodothyronine derivatives or mimetic analogs thereof having at least one of the following characteristics: bromines at the 3',5'-positions; or a rigid linking group which inhibits the interaction of the heavy halogen with the fluorophore. The resulting compounds have high fluorescence, have little if any fluorescent enhancement upon binding to anti-thyroxine and can find use in immunoassays for thyroid hormones or thyroid hormone binding proteins, as well as for fluorescent labeling of thyroid binding proteins.

DESCRIPTION OF THE SPECIFIC EMBODIMENTS

Novel fluorescent compounds are provided having a polyhalothyronine or immunogenic mimetic analog thereof, having at least two iodines and capable of competing with thyroid hormones for proteins specifically binding to thyroid hormones. Particularly, the compounds are 3,5-diiodo-3',5'-dihalo and have at least one of the following characteristics: 3',5'-dibromo substituted; or a rigid linking group between the thyronine or mimetic analog and a fluorophore. The subject compounds are found to be effective in immunoassays for the determination of thyroid hormones or proteins binding specifically to thyroid hormones and have little if any fluorescent enhancement upon binding of an antibody to the thyroid hormone conjugated to the fluorophore.

For the most part, the compounds of this invention will have the following formula:

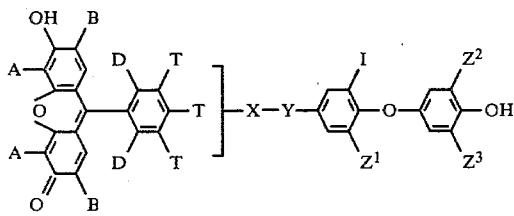

wherein:

A is any group which does not detrimentally affect the fluorescence efficiency or physical characteristics of the compound, particularly water solubility; A will normally be such groups as hydrogen, alkyl, halo, particularly of atomic number 9 to 53, more particularly of atomic number 17 to 35, and substituted alkyl, where alkyl may be substituted with halo as described previously, chalcogen of atomic number 8 to 16 (oxygen and sulfur) as hydroxy, mercapto, oxyether of from 1 to 2 carbon atoms, or thioether of from 1 to 2 carbon atoms, non-oxo-carbonyl, particularly carboxy, alkoxycarbonyl, having alkoxy of from 1 to 2 carbon atoms, or carboxamide, the total number of substituents being normally of from 1 to 4, more usually from 1 to 2, wherein the alkyl groups are from 1 to 6, more usually from 1 to 2 carbon atoms;

B may be the same or different from A, having the same definition of A, and including in addition chalcogen, which includes hydroxy, mercapto, oxyether of from 1 to 2 carbon atoms, and thioether of from 1 to 2 carbon atoms;

D is hydrogen, halo, particularly of atomic number 9 to 80, more particularly of atomic number 17 to 35, and non-oxo-carbonyl, particularly carboxy, alkoxycarbonyl of from 2 to 3 carbon atoms, or carboxamide;

one of the T's is a bond to X, when not a bond, T is hydrogen, non-oxo-carbonyl, particularly carboxy, alkoxycarbonyl of from 2 to 3 carbon atoms, or carboxamide, or halo, particularly halogen of atomic number 17 to 35;

at least two of $Z^{1-3}$ are halogen of atomic number 35 to 53, wherein $Z^1$ is hydrogen or iodine, usually iodine, and $Z^2$ and $Z^3$ may be the same or different, usually the same, and are hydrogen, bromine or iodine;

Y is $(-CO\{(CH\{NH\}_p\{H\})_q(CH_2)_n\}_m-)$, where n is 0 to 2 and m, p and q are 0 to 1, which includes carbonyl, methylenecarbonyl, α-amino-ethylene-carbonyl, etc.

X is a linking group, normally of from 1 to 10 atoms in the chain (all the atoms of a ring being counted), normally having terminal amino nitrogen bonded to Y, having from 1 to 3, usually 1 to 2, nitrogen atoms in the chain, the remaining atoms being carbon and oxygen, particularly carbon, wherein X may be aliphatic, alicyclic, aromatic, or heterocyclic, having from 5 to 7, usually 6, annular members, the total number of heteroatoms varying from 1 to 5, usually 1 to 4, which are nitrogen, as amino or amido, oxygen as oxy, particularly ether, and oxo, particularly as non-oxo-carbonyl, with the proviso that at least when $Z^2$ and $Z^3$ are iodo, preferably when at least one of $Z^2$ and $Z^3$ is iodo, X is an acyclic chain of from 1 to 2 atoms, particularly having carbon and/or nitrogen; or an aromatic, usually carbocyclic, linking group of from 7 to 8 atoms, particularly amino or phenylamino.

Preferred compounds of formula 1 have A as hydrogen or chloro and B as hydrogen, chloro, alkyl of from 1 to 2 carbon atoms, or alkoxy of from 1 to 2 carbons atoms. Usually, the fluorescer portion of the molecule will have 0 to 6, more usually 2 to 6, preferably 2 to 5 halo atoms.

Included within the generic formula is a subgenus, concerned with assays for T-3 or T-4, wherein the only halogen on the thyronine portion is iodo. For the most part, these compounds will have the following formula:

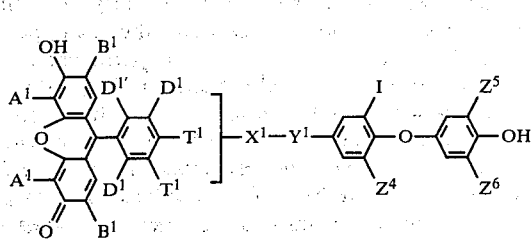

wherein:

A[1] and B[1] may be the same as the A's and B's respectively, but preferably A[1] will be hydrogen or chloro, and B[1] will be hydrogen, chloro, alkyl of from 1 to 2 carbon atoms, particularly methyl, or alkoxy of from 1 to 2 carbon atoms, particularly methoxy;

The D[1]s including D[1]'s may be the same as the D's but preferably D[1] will be hydrogen or halo, particularly chloro, while D[1'] will be hydrogen, halo, particularly chloro, or carboxy;

the T[1]s will come within the same definition of T;

at least two of Z[4-6] are iodo, and when not iodo are hydrogen;

Y[1] comes within the definition of Y, and is preferably carbonyl or methylenecarbonyl;

X[1] is amino, carbonylpiperazinyl or phenyleneamino.

Where the outer halo substituents of the thyronine are bromo, greater flexibility is allowed with the linking group. It is found that the bromine substituents are far less active in catalyzing radiationaless decay as compared to iodine. Therefore, a more flexible linking may be employed, which allows for the dibromohydroquinolyl group to be able to move into close juxtaposition to the fluorophore.

For the most part, the compositions having bromo groups will have the following formula:

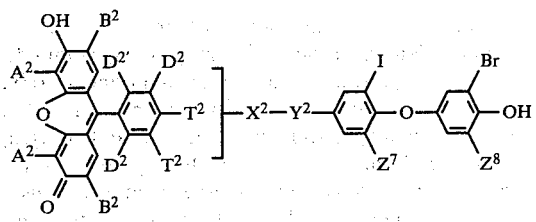

wherein:

A[2], B[2], D[2], D[2'], T[2], and Y[2] come within the definitions for the symbols having the 1 superscript;

at least one of Z[7-8] is halo of atomic number 35 to 53, preferably Z[7] is iodo and Z[8] is bromo, or is otherwise hydrogen;

Y[2] comes within the definition of Y, there being a terminal nitrogen of X[2] bonded to the carbonyl of Y[2];

X[2] is a linking group coming within the definition of X and is usually aliphatic, alicyclic, aromatic or heterocyclic, wherein the rings have from 5 to 7 annular members, X[2] having a total number of atoms other than hydrogen of from 1 to 12, usually 1 to 10, more usually 1 to 8, generally having from 0 to 8, usually 0 to 6 carbon atoms, usually free of aliphatic unsaturation, wherein oxygen is present as oxy or oxo, particularly non-oxo-carbonyl, and nitrogen is present as amino or amido.

Illustrative groups for the symbols A and B are hydrogen, methyl, ethyl, propyl, isopropyl, fluoro, chloro, bromo, iodo, carboxy, carboxamido, methoxycarbonyl, carboxymethyl, chloroethyl, methoxymethyl, hydroxymethyl, and solely for B, methoxy and ethoxy.

Illustrative groups for X include N-carbonyl piperazine, N-carbonyl 1,3-diazole, amino, methyleneamino, carbonylamino, phenyleneamino, benzylamino, p-xylyleneamino, oxyphenylene amino, and ethylene diamino.

Fluorophores described above may be found in copending applications Ser. Nos. 73,158 and 73,163, both filed on Sept. 7, 1979.

The fluorophores can be readily conjugated to the thyronine or the mimetic analogs by conventional means. The fluorophores will normally have various functionalities, particularly non-oxo-carbonyl functionalities, such as isocyanate, carboxy, which can be activated as an active ester, dicarboxylic acid anhydrides, or the like. The carbonyl of the thyronine or mimetic analog may be modified to provide for an amino group which may react with the non-oxo-carbonyl of the fluorophore or the fluorophore may have an amino functionality which may be conjugated with the non-oxo-carbonyl of the thyronine or mimetic analog.

The subject compositions find use in a wide variety of immunoassays requiring a fluorescent label, where the amount of the thyroid hormone or protein specifically binding to a thyroid hormone is related to the amount of fluorescence in the assay medium.

In one technique, the change in fluorescence observed is based on the amount of a receptor which binds to the thyronine or mimetic analog, with resulting reduction in fluorescence. See particularly U.S. Pat. Nos. 3,996,345 and 4,160,818. In these assays, where the thyroid hormone is the ligand, such as T-3, T-4, or inverse T-3, the sample suspected of containing the thyroid hormone is combined with the receptor for the thyroid hormone and the fluorophore conjugate either added at the same time or after a short period of incubation between the receptor and the sample. The fluorescence may then be read after equilibrium has been reached or preferably two readings taken over a short period of time after the addition of the fluorophore, so that the rate of change of fluorescence may be determined. By employing assay media having known amounts of the thyroid hormone, one can relate the change in fluorescence over a period of time with concentration.

An alternative method employs a physical separation between the bound conjugate and the unbound conjugate. Again, one allows for the thyroid hormone in the sample to bind to available binding sites of the receptor, for example, thyroid binding globulin or antibody to the thyroid hormone. One then adds the fluorophore conjugate to bind to any remaining sites of the receptor. One can effect a separation between the unbound and the bound fluorophore conjugate in a number of ways. By further treatment and centrifugation, the bound conjugate will be brought down, and the supernatant retain the unbound fluorophore conjugate. Alternatively, one could bind the receptor to a solid support, such as particles, a plastic strip or the like, and after combining the receptor bound to the solid support with the sample, allow the fluorophore conjugate to bind to any remaining receptor sites. Separation may then be easily carried out by removing the bound fluorophore by centrifugation, physical separation or the like. One may then read the supernatant or the solid support for fluorescence. These techniques may be found in U.S. Pat. Nos. 3,992,631 and 4,067,959.

The following examples are offered by way of illustration and not by way of limitation.

EXPERIMENTAL (All percents and parts not otherwise indicated are by weight except for liquids which are by volume. Temperatures are centigrade. Abbreviations: DCC—dicyclohexyl carbodiimide; NHS—N-hydroxy succinimide; THF—tetrahydrofuran, PEG—polyethylene glycol 6000.)

EXAMPLE 1

N-4-(3',5'-dibromo-4'-hydroxyphenoxy)-3,5-diiodobenzoyl N'-(2',7'-dimethyl-3',6'-dihydroxy-9'-(2'',5'',6''-trichloro-3'' or 4''-carboxyphenyl-4'' or 3''-formyl)xanthene piperazine

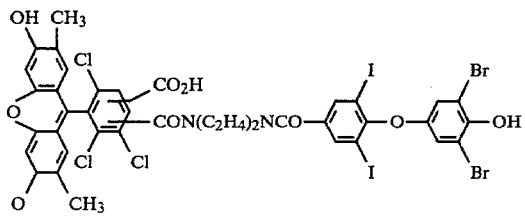

A. To a solution of 550 mg of 3,5-diiodo-4-p-hydroxyphenoxybenzoic acid in glacial acetic acid (0.5 ml) was added bromine (0.7 ml) and stirring continued for 2 hr at room temperature, when a white solid separated out. After filtration, the solid (380 mg) was washed with 5% sodium bisulfite solution (15 ml) followed by water (15 ml) and dried.

B. A solution of 0.5 g of A, 0.138 g of NHS and 0.25 g of DCC in dry THF (3 ml) was stirred overnight, the solution filtered and the filtrate concentrated and dried in vacuo for 15 min. The residue was triturated with hexane (10 ml) and the resulting white solid filtered to give the desired NHS ester (0.58 g).

C. To a rapidly stirring solution of dry piperazine (1 g) in dry THF (150 ml) was added dropwise over a period of 20 min a solution of the NHS ester of B (300 mg) in 5 ml of dry THF. The solution was stirred overnight at room temperature during which time a white solid separated out. The solution was filtered, the solid washed with 20 ml dry THF and recrystallized from chloroform-methanol to provide the pure amide.

D. A solution of 100 mg of a mixture of 2,7-dimethyl-9-(2',5',6'-trichloro-3',4'-dicarboxyphenyl)-3,6-dihydroxy xanthene and 2,7-dimethyl-9-(3',5',6'-trichloro-2',4'-dicarboxyphenyl)-3,6-dihydroxyxanthene and 40 mg of DCC in 3 ml of dry THF was stirred overnight. After filtering the solution, the filtrate was concentrated in vacuo and the residue purified by preparative TLC using cloroform:THF (4:6) as the solvent system. The anhydride was eluted from silica gel with THF to yield 15 mg.

E. To a solution of the anhydride of D (12 mg) in 1 ml of dry DMF containing 50 μl of triethylamine was added 20 mg of the product of C, the solution stirred overnight, and the solvent removed in vacuo. After acidification of the residue with dil. HCl, the mixture was extracted with ether and the ethereal layer purified by repeated preparative TLC to yield 4 mg of the desired product. The product had a $\lambda_{max}^{abs}$ 521–522 nm and $\lambda_{max}^{em}$ 537–38 nm in 0.05 M PO$_4$ buffer, pH8.0. The quantum yield was 73% as compared to D, which was enhanced only by 10% when antithyroxine bound to the thyronine mimetic analog.

EXAMPLE 2

N-4-(3',5'-diiodo-4'-hydroxyphenoxy)-3,5-diiodobenzoyl 2,7-dimethoxy-4,5-dichloro-3,6-dihydroxy-9-(2'-carboxy-4''-amino-m- or -p-biphenylyl-1')xanthene.

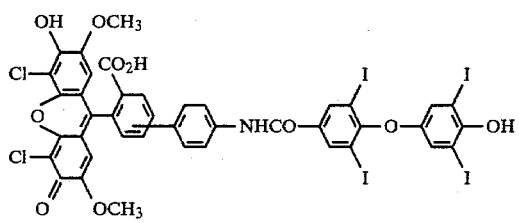

A. A mixture of 3,4-dicarboxy-4'-nitrobiphenyl and 2-chloro-4-methoxyresorcinol was heated at 170° for 5 min, followed by the addition of 150 mg zinc chloride and heating continued for an additional 10 min. After cooling, the residue was dissolved in 4% sodium hydroxide (50 ml), and acidified with stirring to pH1. The resulting dark red solid (∼2 g) was separated by filtration, dried and purified by column chromatography (RP-2 silanised silica gel as adsorbent) and eluted with methylene chloride:acetic acid (100:0.1). The resulting compound had a $\lambda_{max}^{abs}$ 525–26 nm in 0.05 M PO$_4$ buffer.

B. A solution of 50 mg of the above compound (A), 100 mg of sodium sulfide and 60 mg of sodium hydrosulfide in 1.5 ml water was heated at 110° for 30 min, the mixture cooled, acidified with acetic acid and the resulting brown solid filtered. The solid was purified by preparative TLC (CH$_2$Cl$_2$:MeOH:AcOH::90:10:1) to give the product, $\lambda_{max}^{abs}$ 523–24 nm in 0.05 M PO$_4$ buffer.

C. 4-(3',5'-Diiodo-4'-acetoxyphenoxy)-3,5-diiodobenzoic acid was combined with excess thionyl chloride (0.3 ml) and heated for 2 hrs at 60°–65°, followed by removal of the thionyl chloride and drying in vacuo to give the acyl chloride.

D. To a solution of the above product B in 0.5 ml dry pyridine was added a solution of the above product C (50 mg in 0.5 ml pyridine) and the mixture stirred overnight. After removing the pyridine in vacuo at room temperature, the residue was stirred with 2 ml 4% sodium hydroxide for 6 hrs, followed by acidification with dilute HCl. After extracting with ether, the ethereal layer was purified by preparative TLC (CH$_2$Cl$_2$:MeOH:AcOH::80:20:1) and the major fluorescent component eluted from the silica gel with methanol to give the product, $\lambda_{max}^{abs}$ 523–25 nm; $\lambda_{max}^{em}$ 549–50 nm in 0.05 M PO$_4$.

EXAMPLE 3

N-4-(3',5'-diiodo-4'-hydroxyphenoxy)-3,5-diiodobenzoyl 2,7-dimethoxy-4,5-dichloro-9-(2'-carboxy-4'- or -5'-aminophenyl-1')xanthene.

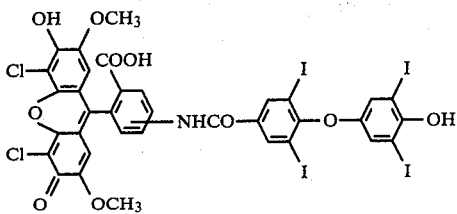

A. A mixture of 4-methoxy-2-chlororesorcinol (1.8 g) and 4-nitrophthalic anhydride (0.85 g) was heated with 30 mg zinc chloride for 5 min at 160°. The workup and purification was as described previously. The resulting product had $\lambda_{max}^{abs}$ 524–25 nm in 0.05 M PO$_4$ buffer.

B. A solution of 50 mg of the above compound A, 100 mg of sodium sulfide and 50 mg of sodium hydrosulfide in 1 ml of water as heated at 100°–105° for 0.5 hr followed by workup as previously described and purification by preparative TLC (CH$_2$Cl$_2$:MeOH:AcOH::85:14:1) to give the product as a mixture, $\lambda_{max}^{abs}$ 515 nm in 0.05 M PO$_4$ buffer.

C. 2,7-Dimethoxy-4,5-dichloro-3,6-dihydroxy-9-(2'-carboxy-4'- or -5'-aminophenyl)xanthene (5 mg) and 30 mg of the acid chloride of 2C in 1 ml dry pyridine were stirred at room temperature overnight, and the mixture worked up as described previously. The resulting product was purified by preparative TLC using the same solvent system as described above providing a product having $\lambda_{abs}^{max}$ 523–525 nm.

EXAMPLE 4

N-(2,7-dimethoxy-3,6-dihydroxy-4,5-dichloro-9-[2'-carboxy-3',6'-dichloro-4'- or -5'-formyl]xanthene) N'-(4-[3',5'-dibromo-4'-hydroxyphenoxy]-3,5-diiodobenzoyl) piperazine.

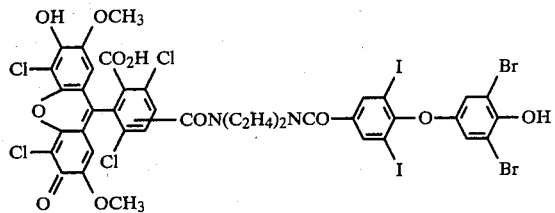

A. A solution of 2,7-dimethoxy-3,6-dihydroxy-4,5-dichloro-9-(2'-carboxy-3',6'-dichloro-4'- or -5'-phenylformyl)xanthene DCC (25 mg) and NHS (13 mg) in dry THF (3 ml) were stirred at room temperature for 4 hrs and worked up as described previously.

B. A mixture of the above ester A (60 mg), and 1C (70 mg) in 2 ml DMF containing 50 μl triethylamine was stirred overnight at room temperature, the solvent removed in vacuo and the residue dissolved in 2 ml 4% sodium hydroxide. After acidification with dil HCl and filtering, the solute was purified by preparative TLC as described previously to provide a product, $\lambda_{max}^{abs}$ 540–41 and $\lambda_{max}^{em}$ 558 nm in 0.05 M PO$_4$ buffer, pH8.0. The quantum yield was about 70% as compared to the fluorescent intermediate prior to conjugation with the polyhalo compound.

EXAMPLE 5

Antithyroxine labeled with 2,7-diiodo-3,6-dihydroxy-4,5-dimethoxy-9-(2'-carboxy-3',6'-dichloro-4'- or -5'-phenylformyl)xanthene.

A. A mixture of 3,6-dichlorobenzene-1,2,4-tricarboxylic acid (280 mg) and 2-methoxyresorcinol (0.4 g) was heated at 190°–195° for 30 min, followed by the addition of 10 mg of zinc chloride and heating continued for 10 min. The product was purified by preparative TLC. $\lambda_{max}^{abs}$ 528 nm in 0.05 M PO$_4$ buffer pH8.0 with no fluorescence emission.

B. A solution of 100 mg of A, 100 mg of iodine and 50 mg of sodium bicarbonate in 2 ml abs ethanol was refluxed for 2 hrs, followed by a second addition of iodine and sodium bicarbonate in the same amounts, refluxing continued overnight, followed by a third addition of iodine and sodium bicarbonate in the same amounts with an additional 8 hrs of reflux. After cooling, the solvent was removed in vacuo, the residue acidified with dil HCl and the organic material taken up in ether. The ether extract (~40 ml) was washed with 5% sodium thiosulfate solution (2×5 ml), brine solution (2×5 ml), followed by water (1×5 ml). The ether was removed and the residue purified by preparative TLC (CH$_2$Cl$_2$:MeOH:AcOH::80:20:1) to give the product $\lambda_{max}^{abs}$ 548 nm in 0.05 M PO$_4$ buffer pH8.0.

C. A solution of 25 mg of the above product B in 1 ml dry THF containing 10 mg DCC and 5 mg NHS were stirred at room temperature for 4 hrs and worked up as described previously.

D. The above product was then combined with antiserum to provide a dye/protein ratio of 7.5. The conjugate had a $\lambda_{max}^{abs}$ 558 nm in 0.05 M PO$_4$ buffer, pH8.0 containing 1% cholic acid.

In order to demonstrate the utility of the subject compounds, a number of studies were carried out where the conjugate of the fluorophore with the thyronine mimetic analog was combined with antithyroxine sera to which had been conjugated a quencher dye capable of quenching the fluorescence of the fluorophore. The amount of quenching was then determined. To demonstrate that the quenching was specific, it was then demonstrated that the amount of quenching could be diminished in the presence of thyroxine. This experiment demonstrates that the subject compositions are useful in assays for thyroxine, since the subject compositions can bind to thyroxine antisera to determine the number of available sites of thyroxine antisera after combining the sample of the thyroid hormone with the antithyroxine sera.

The buffer used in the study was 0.01 M PO$_4$, 0.15 M NaCl and 2% PEG, adjusted to pH8.0. A standard thyroxine (T$_4$) solution was prepared by dissolving 2 mg of commercial T$_4$ in 2 ml of 0.05 M PO$_4$ buffer, pH9.0. An excitation filter of 519 nm and an emission filter of 543 nm was used for quenching experiments with Examples 1–3. For Example 4 the respective filter wavelengths were 543 nm and 569 nm.

A stock solution of the fluorophore conjugate of Example 1 was prepared by employing 25 μl of the UV solution (10$^{-5}$ M) and diluting it with 250 μl of buffer. The antithyroxine-q$_{539}$ stock solution was diluted to give 1:40, 1:20, 1:10, 1:5 and 1:2.5 dilutions of the quencher labeled antithyroxine. Unlabeled antithyroxine and stock solutions of thyroxine (1 mg/ml) were used as such without dilutions. All incubations were carried out for 10 min at room temperature and sensitivity of ×50 was used on the instrument.

With 25 μl of the fluorophore conjugate of Example 1 in a total volume of 2.425 ml buffer, the fluorescence was 755 (avg of 4).

In place of 25 μl of buffer was added 25 μl of the antisera-quencher of the appropriate dilution and duplicate readings taken. The results are reported as averages. At 1:40 diln, fluorescence 650; at 1:20 diln, fluorescence 453; at 1:10 diln, fluorescence 296; at 1:5 diln, fluorescence 181; at 1:2.5 diln, fluorescence 161. With 25 μl of the antithyroxine-quencher alone in a total of 2.425 ml buffer, the background reading varied from 0 to 24 in varying the dilutions from 1:40 to 1:2.5.

Finally, 25 μl of the fluorophore conjugate, 25 μl of T4 standard solution and 25 μl of the antithyroxine-quencher conjugate of appropriate dilution was combined with buffer to a total volume of 2.425 ml and the fluorescence determined. The following are the results:

The fluorescence readings of the various dilutions are indicated as follows: 1:40, 1015; 1:20, 1022; 1:10, 899; 1:5, 832; 1:2.5, 670.

The following, Table I, indicates the results observed with the other conjugates, following the protocol previously described.

TABLE I

| Antibody* Dilution | Conjugate Ex. Fluorescence+ | |
|---|---|---|
| | 3 | 4 |
| 1:40 | 880 | 661 |
| 1:20 | 810 | 574 |
| 1:10 | 637 | 448 |
| 1:5 | 334 | 318 |
| 1:2.5 | 216 | 222 |

*Quencher for conjugate 3 was q539-2',7'-diiodo-4',5'-dimethoxy-6-carboxyfluorescein. Dye/protein ratio 5.2; protein conc. 3.3 × $10^{-5}$M. Quencher for conjugate 4 was q558-2',7'-diiodo-4',5'-dimethoxy-3,6-dichloro-2,4- or 2,5-dicarboxyfluorescein. (See application serial no. 73,163 for method of preparation)

+Fluorescence measured on a Perkin-Elmer Model 1000, measurements at room temperature.

It is found that conjugate 4 has the least nonspecific protein binding of the conjugates. Since thyroxine is found to bind to proteins to a significant degree, due to its hydrophobicity, this adds a further advantage and distinction to the particular conjugate.

The above data demonstrate that the compounds of this invention can be used in immunoassays for thyroid hormones employing a fluorescent signal, particularly for thyroxine, as well as proteins which specifically bind to thyroid hormones, e.g. thyroid binding globulin. The subject compounds absorb and fluoresce at wavelengths substantially higher than serum, so that there is little if any interference from serum background. This is particularly advantageous, when assaying for thyroid hormones in serum, since it minimizes the interference from the endogenous fluorescence resulting from serum proteins.

Although the foregoing invention has been described in some detail by way of illustration and example for purposes of clarity of understanding, it will be obvious that certain changes and modifications may be practiced within the scope of the appended claims.

What is claimed is:

1. A fluorescent compound of the formula

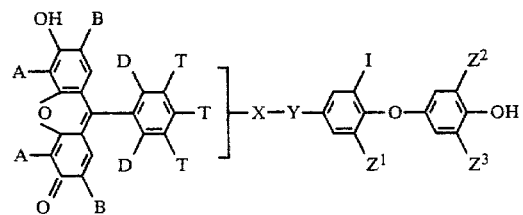

wherein:
A is hydrogen, alkyl, halo, or substituted alkyl;
B is hydrogen, alkyl, halo, substituted alkyl, oxy or thio;
wherein when A and B are alkyl they are from one to six carbon atoms and when substituted alkyl, substituted intends halo, hydroxy, mercapto, oxy-ether or thio-ether of from 1 to 2 carbon atoms, and carboxy;
D is hydrogen, halo, or non-oxo-carbonyl;
one of the Ts is a bond to X, when other than a bond to X, T is hydrogen, non-oxo-carbonyl, or halo;
at least two of $Z^{1-3}$ are halogen of atomic number 35 to 53, wherein $Z^1$ is hydrogen or iodine and $Z^2$ and $Z^3$ are hydrogen, bromine or iodine;
Y is ($-CO\{(CH\{NH\}_p\{H\})_q(CH_2)_n\}_m-$), where n is 0 to 2 and m, p and q are 0 to 1;
X is N-carbonylpiperazinyl.

2. A compound according to claim 1, wherein B is alkyl or alkoxy of from 1 to 2 carbon atoms.

3. A compound according to claim 2, wherein one of the D's is non-oxo-carbonyl.

4. A compound according to any of claims 1, 2 or 3, wherein $Z^2$ and $Z^3$ are bromo.

5. A fluorescent compound of the formula

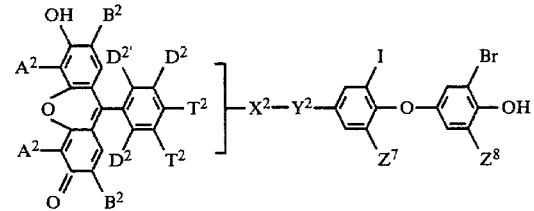

wherein:
$A^2$ is hydrogen, halo or alkyl; from one to two carbon atoms.
$B^2$ is hydrogen, halo, alkyl of from 1 to 2 carbon atoms or alkoxy of from 1 to 2 carbon atoms;
$D^2$ and $D^{2'}$ are hydrogen, halo, or carboxy;
one of $T^2$s is a bond to $X^2$ and when other than a bond, $T^2$ is hydrogen, halo or carboxy;
$Y^2$ is of the formula ($-CO\{(CH\{NH\}_p\{H\})_q(CH_2)_n\}_m-$), where n is 0 to 2 and m, p and q are 0 to 1; and
$X^2$ is N-carbonylpiperazinyl; and at least one of $Z^{7-8}$ is halo of atomic number 35 to 53, or is otherwise hydrogen.

6. A fluorescent compound according to claim 5, wherein $B^2$ is alkoxy of from one to two carbon atoms.

7. A compound according to claim 5, wherein $B^2$ is alkyl of from 1 to 2 carbon atoms.

8. A compound according to any of claims 5, 6 or 7, wherein $Z^7$ is iodo and $Z^8$ is bromo.

9. A compound of the formula

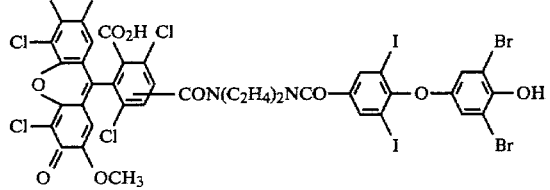

* * * * *